United States Patent [19]
Lokshin et al.

[11] Patent Number: 5,465,608
[45] Date of Patent: Nov. 14, 1995

[54] SAW VAPOR SENSOR APPARATUS AND MULTICOMPONENT SIGNAL PROCESSING

[75] Inventors: Anatole Lokshin, Claremont; David E. Burchfield, Rancho Cucamonga, both of Calif.; David H. Tracy, Norwalk, Conn.

[73] Assignee: Orbital Sciences Corporation, Dulles, Va.

[21] Appl. No.: 85,604

[22] Filed: Jun. 30, 1993

[51] Int. Cl.⁶ .................................................. G01N 29/02
[52] U.S. Cl. ........................................ 73/24.01; 364/498
[58] Field of Search ................................ 73/24.01, 24.06, 73/23.2, 31.01, 31.02, 579; 364/498

[56] References Cited

U.S. PATENT DOCUMENTS

| | | | |
|---|---|---|---|
| 3,333,192 | 7/1967 | Geyger | 324/117 |
| 4,312,228 | 1/1982 | Wohltjen | 73/597 |
| 4,660,151 | 4/1987 | Chipman et al. | 364/498 |
| 4,807,148 | 2/1989 | Lacey | 73/23.36 X |
| 4,888,295 | 12/1989 | Zaromb et al. | 73/31.02 X |
| 4,895,017 | 1/1990 | Pyke et al. | |
| 5,076,094 | 12/1991 | Frye et al. | 73/240.01 X |
| 5,243,539 | 9/1993 | Holt et al. | 73/23.2 X |
| 5,313,416 | 5/1994 | Kauppinen et al. | 364/498 |
| 5,325,705 | 7/1994 | Tom | 73/23.2 X |
| 5,351,198 | 9/1994 | Adachi et al. | 364/498 |

OTHER PUBLICATIONS

W. Patrick Carey and Bruce R. Kowalski, "Chemical Piezoelectric Sensor and Sensor Array Characterization," Anal. Chem. 1986, 58, pp. 3077–3084.

Susan L. Rose–Pehrsson, Jay W. Grate, David S. Ballantine, Jr. and Peter C. Jurs, "Detection of Hazardous Vapors Including Mixtures Using Pattern Recognition Analysis of Responses from Surface Acoustic Wave Devices," Anal. Chem. 1988 60 pp. 2801–2811.

Primary Examiner—Thomas P. Noland
Attorney, Agent, or Firm—Jenner & Block

[57] ABSTRACT

A method and apparatus for the identification and quantification of a vapor, or a number of vapors, in air mixtures is discussed. The method includes calibration of a vapor responsive sensor, or a plurality of vapor responsive sensors, to known concentrations of the vapors of interest or to known concentrations of potential interfering vapors. The calibrations result in sensor response vectors which are derived from the transient signals observed as the vapors are sorbed and desorbed on the sensors. Detection of vapors in complex mixtures is effected by subjecting the apparatus to the mixture and measuring the sensor response, or plurality of sensor responses, and then applying multidimensional statistical analysis or filtering methods to this data, using the precalibrated response vectors as the basis set for deconvolution. The sensors disclosed are Surface Acoustic Wave sensors (SAWs), and include variations of temperature programmed SAWs, SAWs with various combinations of chemically selective coatings, and arrays of temperature programmed and coated SAWs.

13 Claims, 7 Drawing Sheets

SAW VAPOR SENSOR APPARATUS AND MULTICOMPONENT SIGNAL PROCESSING

BACKGROUND OF THE INVENTION

1. Field of Invention

The identification and quantification of a chemical vapor in a vapor mixture by the physical parameters of a sensor which change upon exposure to the vapor mixture.

2. Prior Art

[1] W. Patrick Garey, Bruce R. Kowalski, "Chemical Piezoelectric Sensor and Sensor Array Characterization", Anal. Chem. 1986, 58, 3077–3084.

[2] Susan L. Rose-Pehrsson, Jay W. Grate, David S. Ballantine, Jr., Peter C. Juts, "Detection of Hazardous vapors Including Mixtures Using Pattern Recognition Analysis of Responses from Surface Acoustic Wave Devices", Anal Chem 1988, 60, 2801–2811.

[3] Pyke et al., "Apparatus and Method for Early Detection and Identification of Dilute Chemical Vapors", U.S. Pat. No. 4,895,017, Jan. 23, 1990.

This invention relates to an apparatus and method for sensing and identifying the chemical vapor and resolving a chemical composition of a vapor mixture and is specifically directed to an apparatus and method which uses the physical parameter changes of a sensor when exposed to the vapor mixture to identify a particular compound in the chemical vapor mixture, and to determine concentration of one or more components in the mixture. This invention includes a method for discriminating instrument responses to chemical vapors from instrument noise and chemical interferant noise sources.

This invention will be explained in connection with the use of Surface Acoustic Wave (SAW) sensors but it should be understood that this invention may be used with any sensor which will react upon exposure to a chemical vapor.

While some of the definitions hereinbelow are prior art, for the purposes of facilitating the description of this invention, the following definitions will apply:

SAW sensor—a pair of SAW oscillators (SAWs). One, called sample SAW is coated with a selected coating material and periodically exposed to the sample air and another, called reference SAW, is not coated or, if coated, is not exposed.

SAW signal—one cycle difference in frequency oscillation between a sample and a reference SAW, i.e., the measurement of oscillation frequencies as the SAWs are first exposed to clean air, then subjected to a contaminated atmosphere, and finally re-exposed to clean air.

SAW array—a set of several SAW sensors with different coatings on the sample SAWs or a set of several SAW sensors having the same coating or different coatings or any combination of coatings on the sample SAWs with each SAW sensor held at the same temperature or at different temperatures from the others.

Compound—a chemical that can produce a non-negligible signal on a SAW sensor.

Target Compounds—those chemicals whose presence or concentrations need to be determined in an air stream, and to which a selected SAW sensor is designed to be responsive.

Contaminants—compounds other than target compounds present in the sample air stream, also called interferants.

Mixture—all the compounds contained in the sampled air stream.

Noise—a signal observed when the sample air stream and a reference air stream are the same air. Also, a signal, either instrumental or caused by an interferant in the sampled air, that may be interpreted as a target compound response.

Sensitivity—Signal-to-noise ratio at a signal produced by a unit concentration of a compound of interest. For the fingerprint method, it is an amplitude of the steady state part of a signal produced by a unit concentration.

Characteristic transient, characteristic response of a chemical—noise free, one cycle signal (or any part of thereof) produced by a unit concentration of this chemical at a given SAW.

Characteristic spectrum of a chemical—a vector consisting of the characteristic transients from all the sensors of a SAW array.

It is recognized that a SAW measures air concentrations of a particular compound by changing its resonant frequency in the presence of additional mass on the coated SAW surface. The target compound sorbs into a selective coating on the surface of the SAW, equilibrating the activity (or concentration) of the compound in the coating film with the activity (or partial pressure) of the target compound in the air. The resulting frequency shift is proportional to the added surface mass density at a steady state equilibrium [1]. To allow multiple measurements, the coating material needs to have a reversible response, namely, after a target compound is removed from the air stream, the frequency shift (between the coated and uncoated SAWs) should return to zero (only with the baseline removed) as the target compound desorbs from the SAW coating. Therefore, SAW sensor measurements are done in cycles where a SAW sensor is exposed alternately to analyzed and reference (nominally uncontaminated) air streams. A typical SAW sensor output signal is shown in FIG. 4.

Each measurement cycle, as shown in FIG. 6, (which is one of the measurement signals in FIGS. 4 and 5) has a loading phase (curve A) when a compound penetrates into the coating, a steady state phase (curve B) when compound concentration in the coating reaches equilibrium with t e compound concentration in the air above the coating, and an unloading phase (curve C) during which the chemical is washed out of the surface coating by a stream of reference air. The loading and unloading phases are present in any cycle, but a steady state phase sometimes is not reached because the exposure time of the SAW coating to a chemical is too short compared to the mass transport and diffusion rates for that chemical in the system.

Different coatings may have different sensitivities toward different compounds. When it is possible to find a set of coating materials with very high selectivity toward particular compounds, then a SAW array comprising more than one SAW sensor with different coatings on the sample SAW of each SAW sensor can resolve a mixture of several compounds. The normal arrangement of a SAW array is to have almost as many SAW sensors as there are different compounds in the mixture with each sample SAW possessing a different coating with a high selectivity toward one of the compounds in the mixture.

It is to be understood that a SAW array may be a set of more than one SAW sensor, each with the same coating, or different coatings, or a combination of coatings on the sample SAWs, and which are held at the same temperature or at different temperatures so as to be sensitive to each of the compounds of interest. The steady state response of a SAW array to each of the compounds of interest is called the compound's "fingerprint" on this particular SAW array.

Currently, there are two major methods for processing SAW data.

A. Fingerprint Method: one data point per SAW

The existing SAW sensors use a steady state frequency shift of one measurement cycle (curve B in FIG. 6). Then a maximum of frequency shift (FIG. 7), or an integral of a one cycle frequency shift (FIG. 8), is used. This produces one data point per SAW sensor per measurement cycle.

The current state of the art uses N-dimensional cluster analysis to separate target compound signals from those signals due to contaminants or interferants [2]. By significant computational efforts, it is often possible to increase the number of possible contaminants (using the same number of SAW sensors) by 20% to 30%. Usually, several similar contaminants are grouped into one class by observing that their "fingerprints" occupy the same region in an N-dimensional space.

The cluster analysis method is computationally expensive and does not give significant savings in the number of SAW sensors needed for multicomponent separation.

Also, the method discriminates compounds based on their steady state responses on the SAW array. This need for a steady state response requires a measurement time which is long, especially for small concentrations of the components of interest.

B. Analysis based on Time Constant Determination

An alternative method [3], instead of relying exclusively on the steady state (static) characteristic, tries to make use of some dynamic information. The method introduces one more parameter—the target compound sorption time constant $\tau$. This method relies on an explicit sorption model $$M(t) = 0.9 \cdot M_0 \cdot (1 - e^{-R \cdot t}) \left[ (1 - e^{-\tau \cdot t}) + \frac{1}{9} (1 - e^{-9\tau \cdot t}) \right] \quad (1)$$

where $M_o$ is the mass sorbed at a steady state, and R is a constant depending on a rate of air flow. In this case, each SAW sensor produces two data points that are characteristic for a given compound and its concentration: diffusion time constant $\tau$ and a steady state sorption $M_o$. Since an explicit form of an sorption transient is used, both characteristic constants $\tau$ and $M_o$ can be determined before a steady state is achieved. This allows a reduction in measurement time and provides an early determination of a target compound concentration before a steady state response is reached. In addition, the sorption time constant gives an extra degree of freedom to determine which component is present in the air stream.

However, the time constant method requires the SAW coatings to have a very selected sensitivity to the target compounds. When several compounds are present, equation (1) becomes a sum of several exponents:

$$M(t) = \sum_k 0.9 \cdot M_{0_k} \cdot (1 - e^{-R_k t}) \left[ (1 - e^{-\tau_k t}) + \frac{1}{9} \cdot (1 - e^{-9\tau_k t}) \right] \quad (2)$$

Equation (2) has 3×K unknown parameters: $M_{ok}$, $R_k$, $\tau_k$: k=1 ... K; where K is the number of different compounds in the air stream. M (t), the mass of analyts sorbed at time t is nonlinear with respect to unknown parameters and becomes unmanageable for large K. Since the instrument response is to first order linear with sorbed analyt mass, the complex behavior of mixtures leads to unmanageable data analysis.

SUMMARY OF THE INVENTION

An object of this invention is to decrease the number of different SAW sensors necessary for mixture resolution, to relax the requirement for high steady state selectivity for each coating, and to significantly improve the overall sensitivity of the system.

This invention involves the calibration of a selected sample SAW of a SAW sensor with respect to the target compound and the detection and quantification of the target compound in a gas mixture by the use of the SAW sensor. This also allows a mixture resolution by using a number of calibrated SAW sensors smaller than the number of different compounds in the analyzed mixture.

In the calibration mode, an average one cycle response of a SAW sensor to a particular target compound is determined by directing a mixture having a known concentration of this particular target compound over the sample SAW. The output from this SAW sensor is processed for each target compound to provide a set of vectors $x_i$ wherein each vector represents an average one cycle response per unit concentration of the i-th target compound. These vectors are called "characteristic transients". The vectors $x_i$ make up the columns of the calibration matrix X, defining the instrument response to all compounds of interest.

In the detection mode, a mixture having compounds of unknown concentrations can be determined using a single calibrated SAW or a SAW array comprising the plurality of the previously calibrated SAW sensors and by applying multidimensional statistics or filtering methods to the output of the single calibrated SAW or calibrated SAW array.

This invention does not rely solely on the steady state frequency shift as in the "fingerprint method" or on an explicit model of the sorption process as in the "time constant" method. This invention instead uses an overall transient shape, or a part thereof, to resolve a particular gas mixture. The transient response is determined by the instrument, and is defined as the instrument transfer function convolved with the compound concentrations. Stated another way, this invention uses the whole or a part of a one cycle frequency shift as an n-dimensional vector data and then applies any of the known methods, such as multidimensional statistical methods and/or linear or non-linear filtering methods to this data to resolve a multicomponent mixture.

As will be apparent to those skilled in the art, this invention, when compared to the fingerprint method, is an improvement thereover in that:

a. Instead of a one data point per cycle, this method uses a vector which represents the whole cycle or a part thereof. Therefore, a mixture can be separated by using fewer SAW sensors since the method increases dimensionality of the sampling space, b. There is no need to wait for a steady state response, and c. There are much milder requirements on selectivity of the individual SAW sensors since there are more degrees of freedom in the data obtained with the fingerprint method which has one degree of freedom per SAW sensor.

As will also be apparent, this invention, when compared to the time constant method, is an improvement thereover in that this invention:

a. does not use any parametric model for the physical phenomena, b. uses the whole cycle or any part of it instead of a loading phase only, c. uses a characteristic spectrum of a mixture which is a linear combination of the characteristic spectra of the individual components while a time constant of a mixture is not a linear combination of the individual time constants, d. does not require a high selectivity of the SAW coating, e. provides a number of degrees of freedom per SAW and is not predetermined to 2 but can be determined from the available data, e.g., via Singular Value Decomposition of a calibration matrix X, f. complicated mixtures can be separated using a fewer number of SAW sensors, and g. there is no need for a parameter estimation procedure.

DETAILED DESCRIPTION

Figure 1:
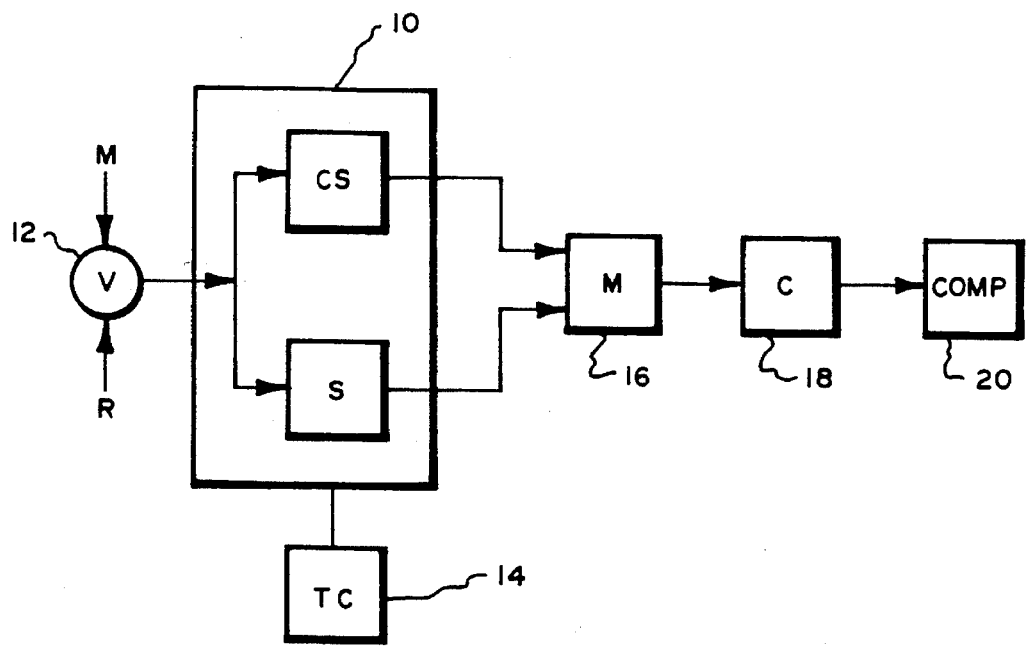
FIG. 1 is a block diagram of a SAW sensor for calibration of the sample SAW and/or for detection of target compound in a gas mixture using the calibrated sample SAW.

FIG. 1 illustrates a SAW sensor 10 which comprises a coated SAW CS and an uncoated SAW S. The input to both SAWs comprises a valve 12 for the supply of a vapor mixture M and an uncontaminated air supply R so that the vapor mixture M and/or the uncontaminated air R (reference air) may be directed alternately to both SAWs. Directing the flow of mixture M and reference air R through both SAWs alternately takes care of any changes in such parameters as air temperature, in flow rate, etc. The SAW sensor 10 is coupled to a suitable temperature control device 14 to regulate its temperature and the temperature of mixture M and reference air R flowing therethrough. The output of each SAW is connected to a differential mixer 16 which in turn is connected to a counter 18 and the latter's output is directed to a computer 20.

The SAW sensor 10 is used for determining a one cycle response to a unit concentration of a target compound. For calibration purposes, a known concentration of a i-th target compound in mixture M is directed to both SAW sensors through valve 12 and thereafter the uncontaminated air R is directed through valve 12 to both sensors. The oscillation frequency of the SAWs in response to the mixture M and the uncontaminated air R provide the frequency shift by reason of the sorption of the target compound by the coating on the sample SAW CS and this frequency shift is directed to the mixer 16 which produces a difference frequency. Counter 18 samples this difference frequency and produces an output signal which is processed in the computer to form a set of vectors. An average one cycle vector response $x_i$ scaled for a unit concentration of the target compound is called the "characteristic transient" of the target compound for a particular SAW sensor and, since there is no a priori assumptions about the form of the response of a SAW sensor having a calibrated SAW to unit concentration of the target compound, the calibration process takes into account hardware peculiarities and possible deviations from a theoretical model as described in [3].

Figure 2:
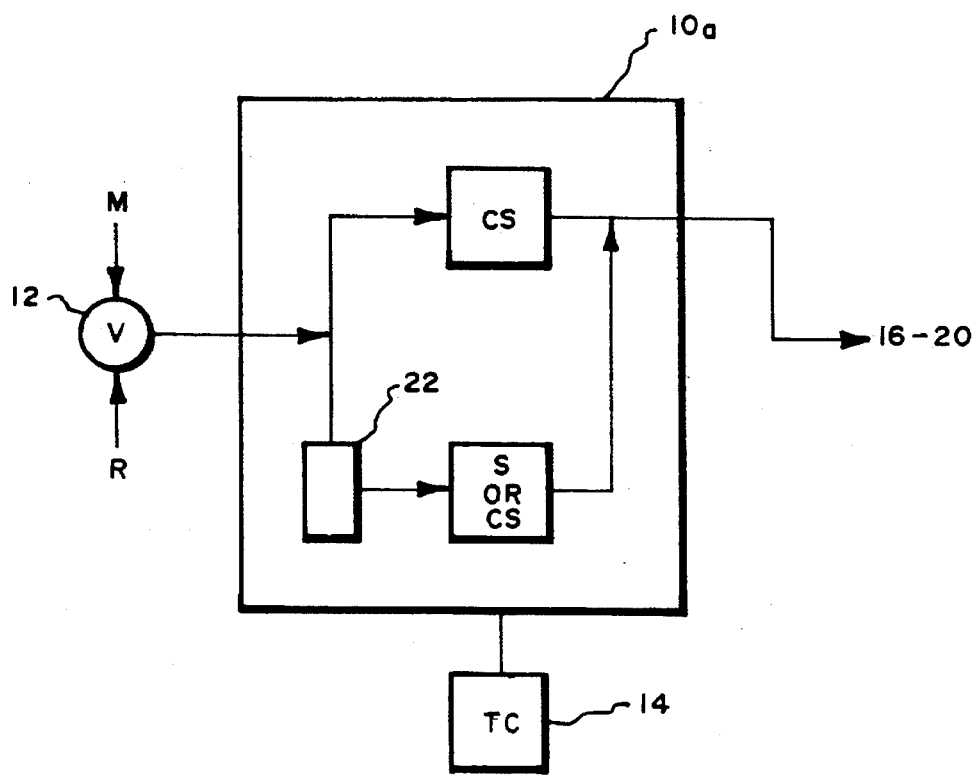
FIG. 2 is a block diagram of a SAW sensor with one coated SAW exposed to the sampled air, and the second SAW, either coated or uncoated, exposed to air filtered to remove contaminants.

FIG. 2 shows a SAW CS sensor 10a with one SAW subject to the mixture and reference air while the other SAW, S or CS, is subject only to the temperature, pressure and flow rate of the mixture and reference air. The input of this latter SAW is directed through a filter 22 where the target compound is removed. The advantage gained hereby is that a coated reference oscillator can more effectively null temperature sensitive viscosity changes caused in the sampling SAW by sample air temperature gradients.

SAW sensor 10 (or SAW sensor 10A as the case may be) is calibrated for all the target compounds and potential interferants that could be expected to be in the mixture.

For example, for the target compound TBP and the interferants water and acetone, a calibration matrix is constructed of characteristic response vectors $x_i$ for each of the three compounds:

$$X = [x_{TBP}, x_{H2O}, x_{ACET}] \qquad (3)$$

Then a mixture with concentration $$c = [c_{TBP}, c_{H2O}, c_{ACT}] \qquad (4)$$

will produce a SAW signal $$Y = x \cdot c \qquad (5)$$

Other SAW sensors in the array are similarly calibrated.

Figure 3:
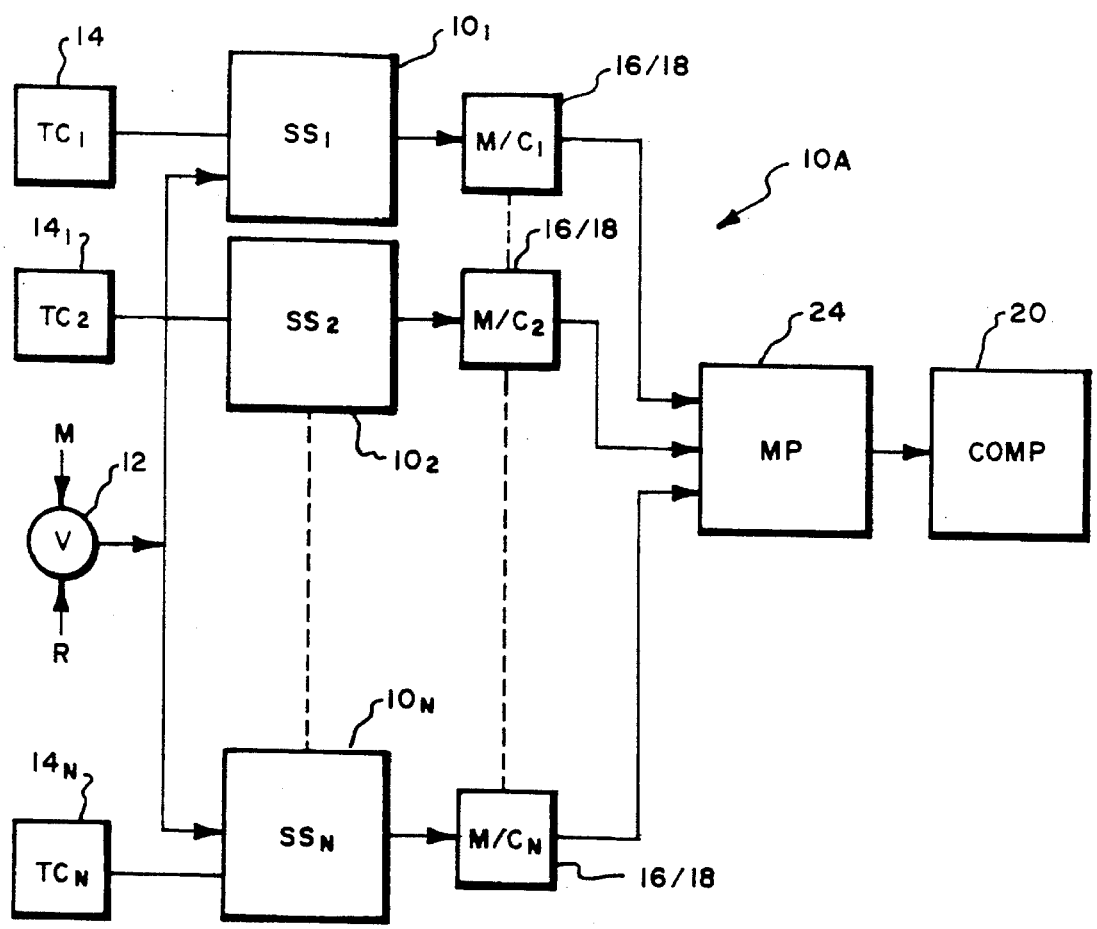
FIG. 3 is a block diagram of a SAW array comprising a set of SAW sensors with sample SAWs of the same or different coatings or a combination of coatings with each SAW sensor being held at the same or different temperatures.
Figure 3A:
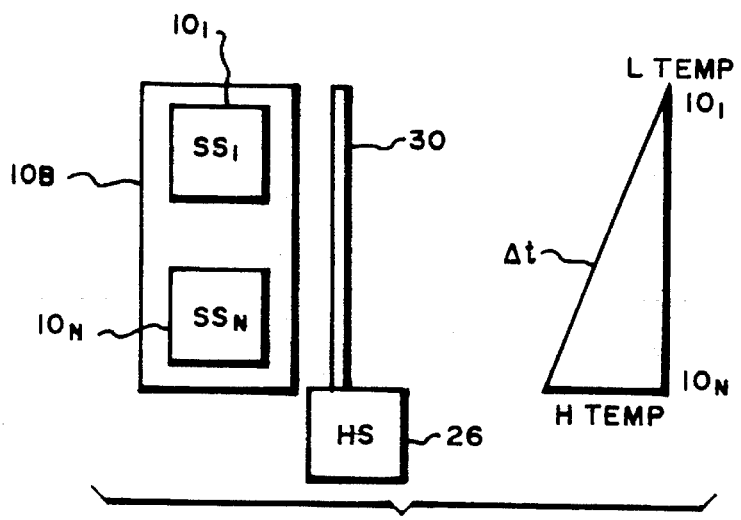
FIG. 3a is a block diagram of a SAW array with a heat conductive bar to provide a linear temperature gradient heat control.

FIG. 3 illustrates a SAW array 10A which contains a calibrated SAW sensor $10_1$ ($SS_1$) in combination with a plurality of SAW sensors, designated as $10_1$–$10_N$ ($SS_1$–$SS_N$), and with a plurality of temperature controls, designated as $14_1$–$14_N$. These temperature controls function to control the temperatures of each SAW sensor and the mixture and reference air as above described. Since the SAW sensors may have the same or different coatings, these temperature controls provide a wide variety of temperature control over multiple SAW sensors in the array 10A.

Where a complex heating arrangement is not required, a SAW array 10B such as shown in FIG. 3a, will utilize a heat source 26 and a heat conductive bar 30 to provide a linear temperature gradient across the array 10B to control its temperature.

Turning back to FIG. 3, it can be seen that the output of each SAW sensor $10_1$–$10_N$ is directed first to a mixer and counter, shown combined and designated M/$C_1$–M/$C_N$ and 16/18. The output signals from each mixture and counter combination is then directed to a multiplexer 24 whose output signals are processed to form a set of vectors $x_i$ in computer 20.

Figure 4:
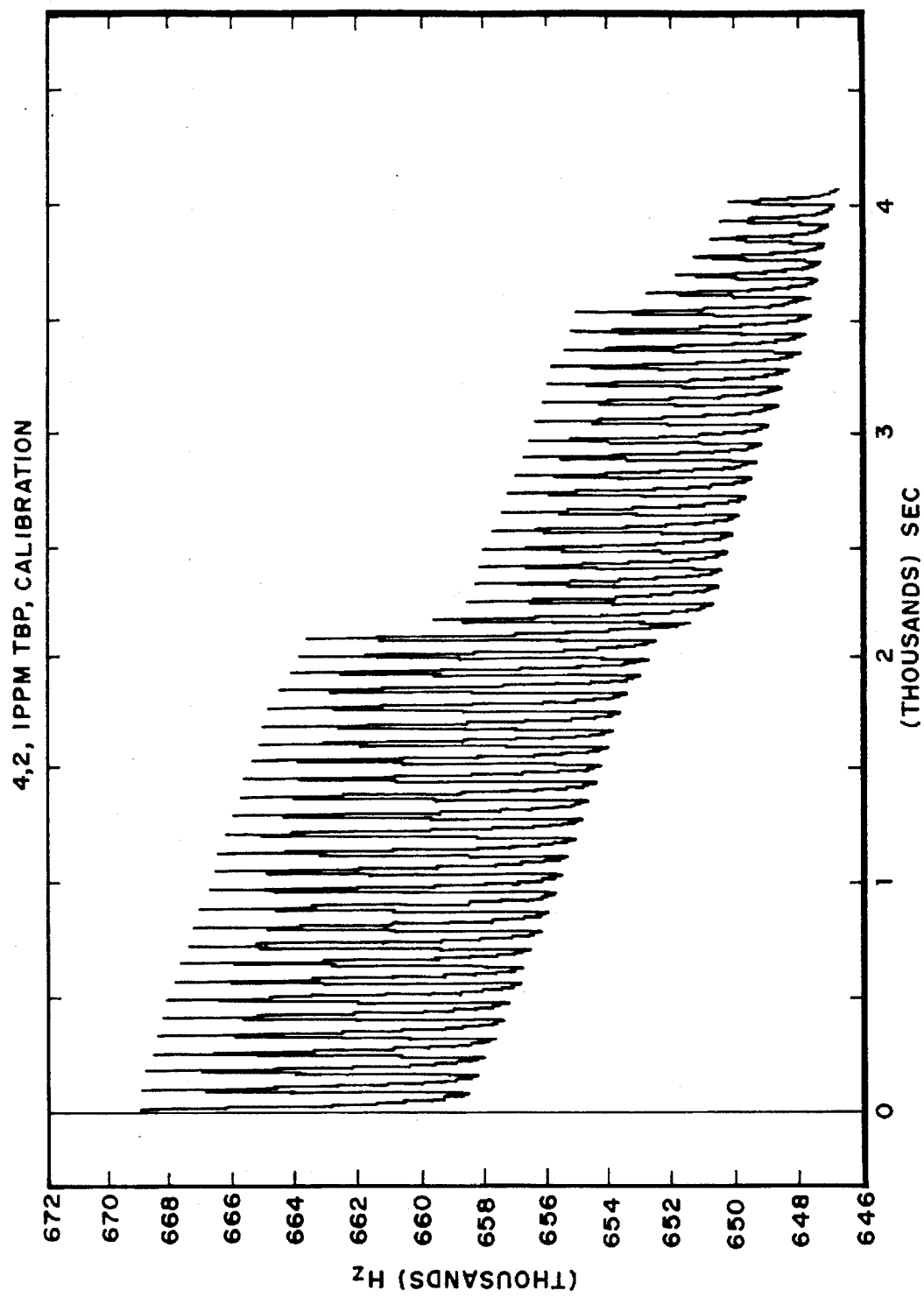
FIG. 4 shows the raw SAW sensor output signal for TBP (tributyl phosphate) vapors of three concentrations.
Figure 5:
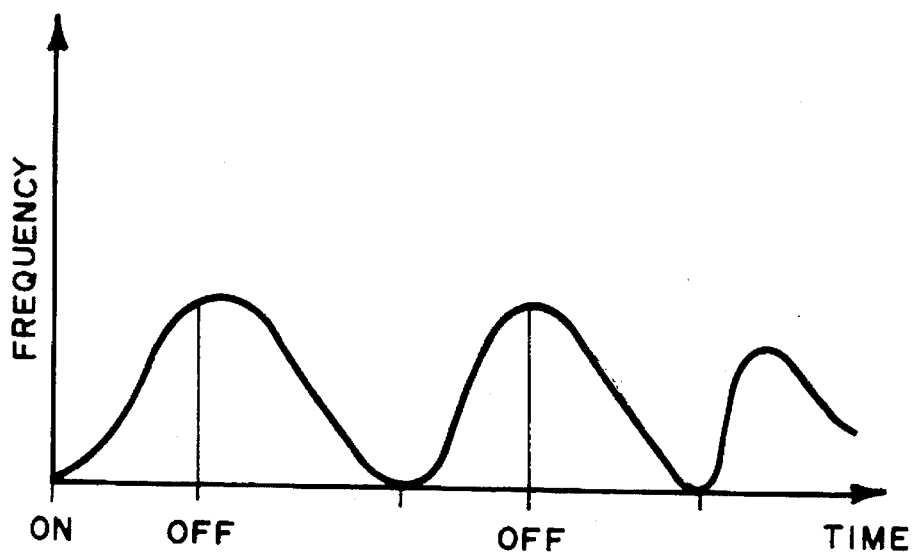
FIG. 5 shows the SAW output signal of FIG. 4 with the baseline drift removed.
Figure 6:
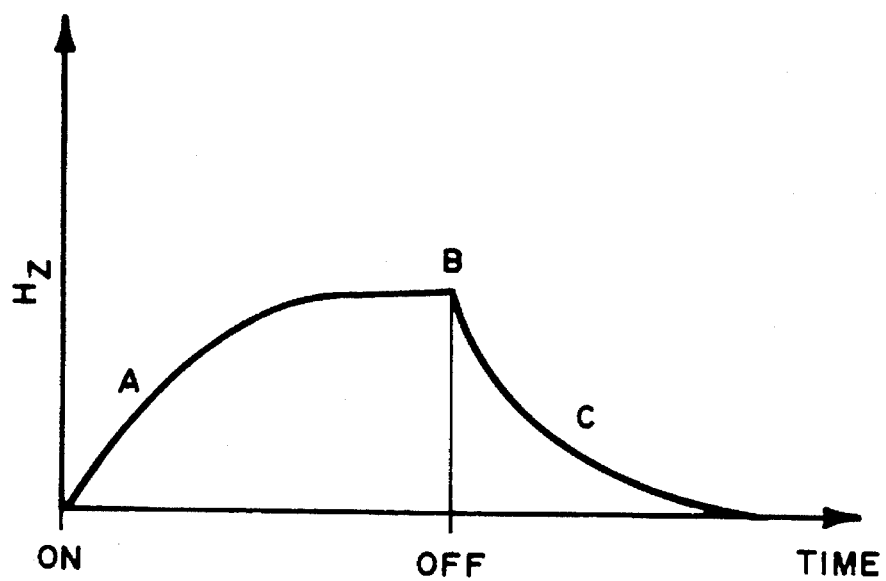
FIG. 6 is a typical one cycle signal with a baseline removed, i.e., one cycle of the signal of FIGS. 4 and 5.

Turning now to FIGS. 4–12 to explain the detection mode, it is pointed out that FIGS. 4–6 were previously referred to in the Background but will again be discussed to shown the ability of this invention to identify a target compound and its concentration in a mixture.

Again, FIG. 4 represents raw data, shown as the cyclical output signal from a single SAW sensor in response to TBP, the target compound of interest. FIG. 4 is a plot, frequency versus time, representing the frequency shift signal as the output from this SAW sensor in response to different concentrations of TBP, for example, concentrations of 1, 2 and 4 ppm. Any one of these cycles may be used for analysis and FIG. 5 is a rough sketch of this same data to show how the output signal of FIG. 4 appears with the baseline removed.

FIG. 6 is also a rough sketch of one of the cycles of FIG. 5 to show the various phases of the signal. As explained before, each measurement cycle has a loading phase (curve A) when the mixture penetrates the coating on the sample SAW, a steady state phase (curve B) when the mixture concentration in the coating reaches equilibrium with the mixture concentration in the air above the coating, and an unloading phase (curve C) during which the mixture is washed out of the coating by a stream of reference air. Again, each cycle in FIGS. 4, 5 and 6 contain these phases if the exposure time of the SAW coating to the target compound is not too short.

The following figures show the difficulty of identifying a target compound, such as TBP, in a mixture by the prior art methods.

Figure 7:
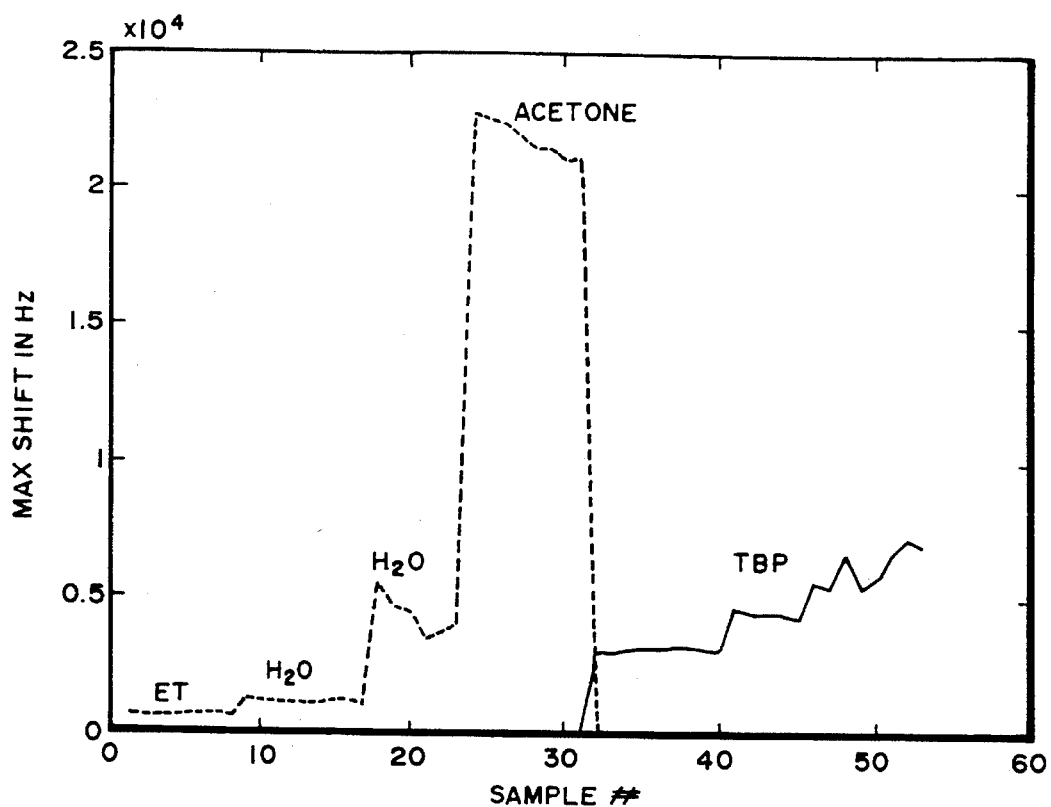
FIG. 7 shows the sensor response to ethanol, water, acetone, and TBP vapors using the method of steady state frequency shifts. Component identification based on maximum of a single cycle shift is not possible with this sensor.

FIG. 7, a plot of maximum signal shift versus sample number, shows signal separation by maximum frequency shift induced by different concentrations of different vapors. This figure shows data for water vapors, ethanol, acetone and various concentrations of TBP with acetone having the strongest signal and ethanol and TBP barely distinguishable from the water vapor. This figure also shows the inability of distinguishing the various vapors in a mixture if only the maximum values of the curves are considered.

Figure 8:
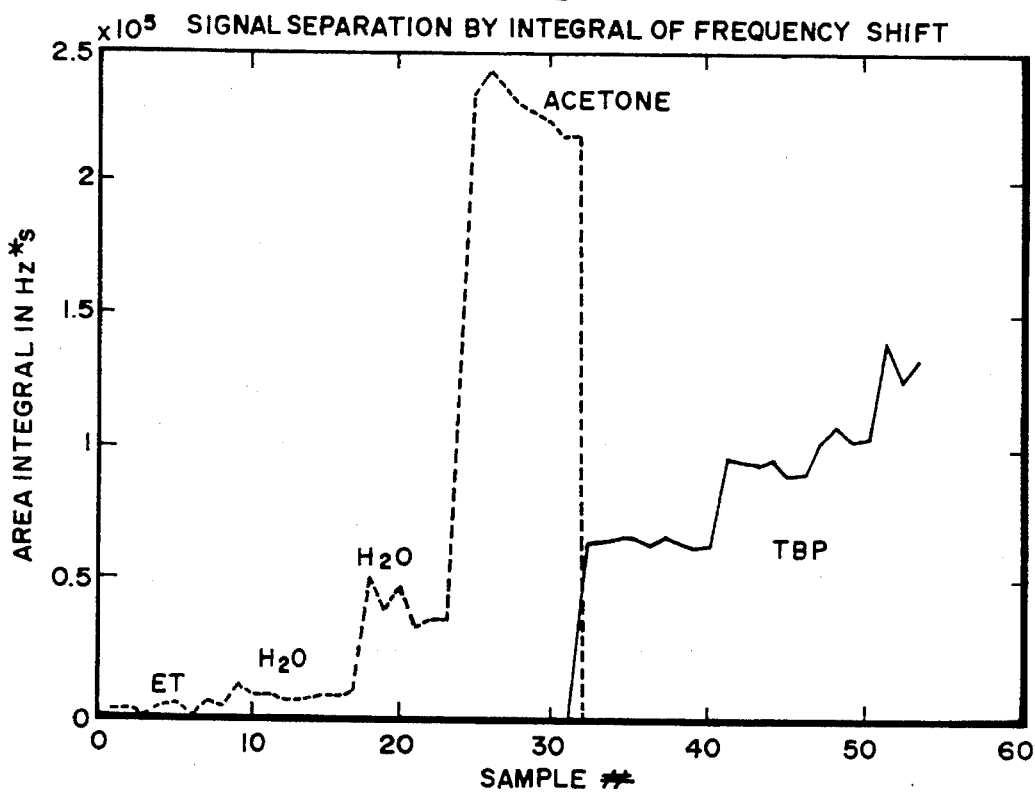
FIG. 8 shows signal separation by the integral of frequency shifts, also illustrating an inability to resolve TBP from the other interferants.

FIG. 8, a plot of signal separation by integral of frequency shift vs sample number, shows that this method produces substantially the same in result as in FIG. 7.

Both of these figures are derived from signals, as shown in FIG. 6, collected from experiments where the different vapors were measured separately on one sensor.

Figure 9:
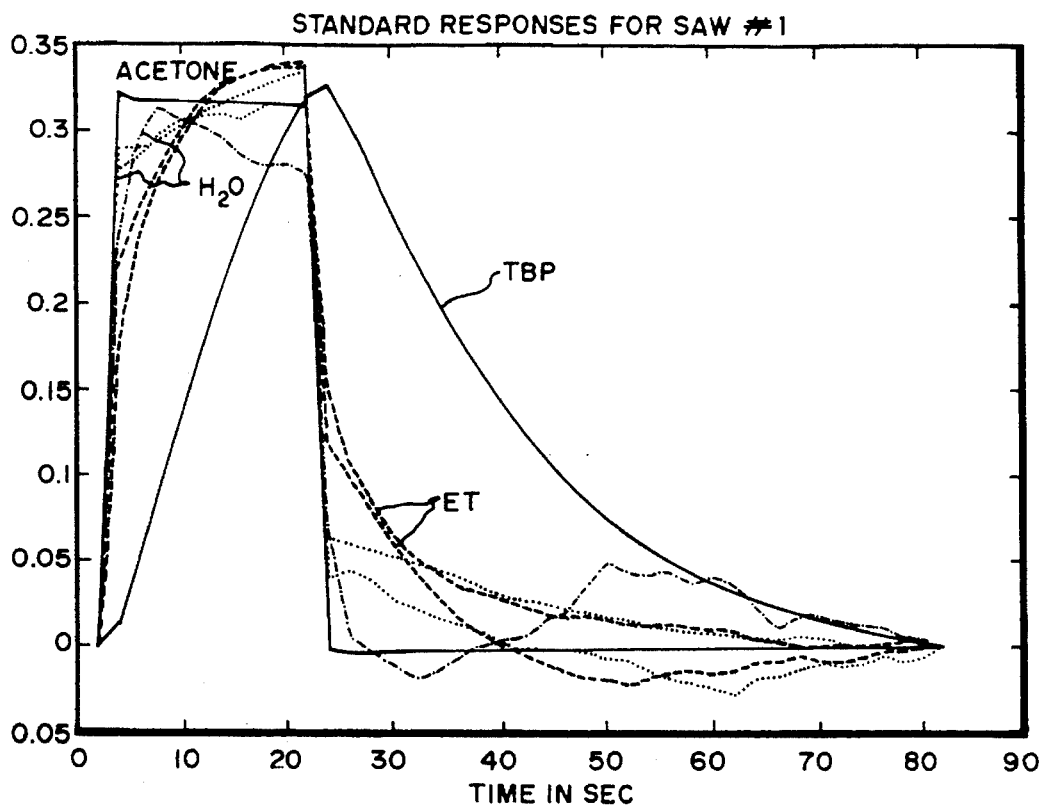
FIG. 9 shows that different components have different characteristic transients (normalized signals)

The cyclical curves of FIGS. 4, 5 and 6 show the output of a single SAW sensor in response to TBP during the calibration step and the calibration of other SAW sensors for other target compounds will produce cyclical curves of different shapes as seen in FIG. 9 which shows the output curves for the same vapors as in FIG. 7, ethanol, water, acetone and TBP.

FIG. 9 is a plot of frequency shift vs. time and is similar to FIG. 6 with different vapors shown overlaying each other. Note the different shapes of the various vapors. The shape of the curve representing TBP differs from the shape of the curves of the other vapors. The amplitudes are normalized to have unit area under the curves. Were the other vapor curves shown alone, their cyclical curves would be represented as such in a curve such as in FIG. 6, with unique transient responses characterizing the loading and unloading phases of that curve.

Figure 10:
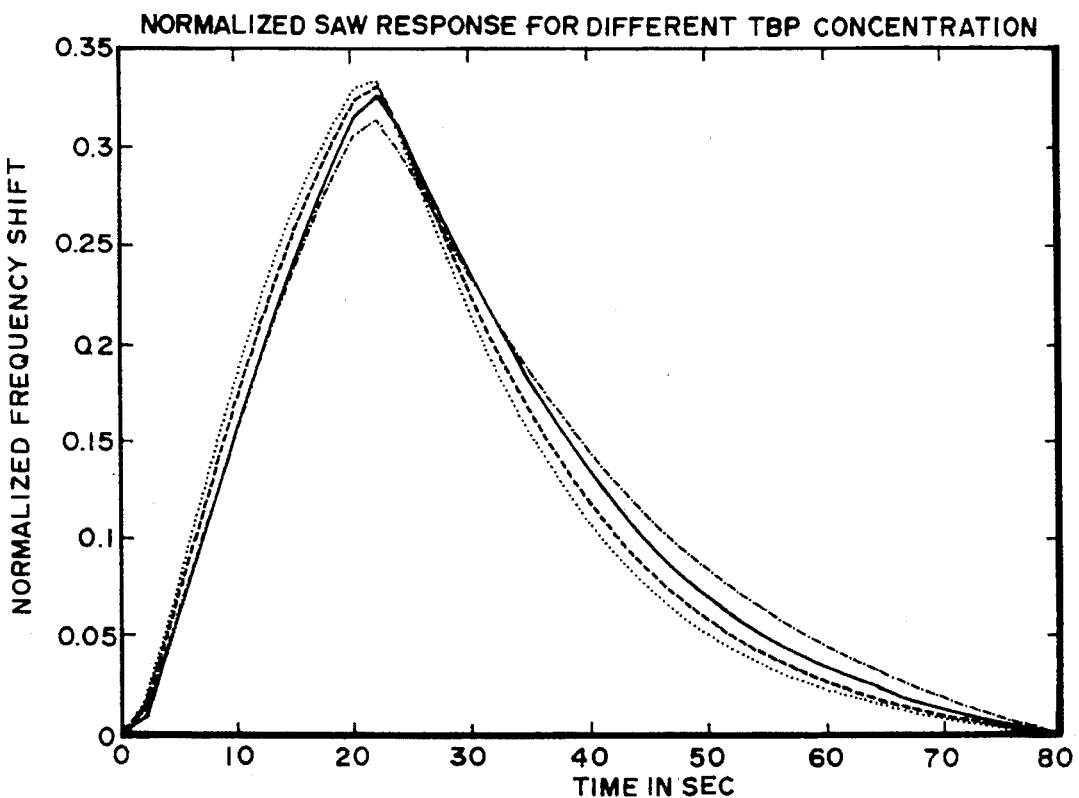
FIG. 10 shows a normalized SAW response for different TBP concentrations which shows that transient shape does not depend on concentration.

FIG. 10 is a plot of frequency shift vs. time and shows a SAW sensor response to different TBP concentrations normalized to a unit area. This FIG. demonstrates that the shapes of the curves do not depend on the concentration of TBP. It is apparent that different components have different transient responses irrespective of concentration and this important discovery enables the target compound to be identified in the mixture.

Thus, in the detection mode, a mixture having compounds of unknown concentrations can be determined by standard methods of multidimensional statistics-linear or nonlinear. For example, a Least Squares fit can be used as:

$$c = X^+ \cdot y \qquad (6)$$

where vector c gives concentrations of each component in the mixture, vector Y represents one cycle SAW frequency shift and matrix X is built during the calibration stage, with columns comprised of the standard response vectors $x_i$ for each of the i components of the mixture. $X^+$ denotes a pseudo inverse of the calibration matrix X, and is effectively a weighting vector for extracting component concentrations from the instrument response Y=y(t).

A similar method can be applied to an array of SAWs with different coatings by simply assembling the characteristics transients $x_i$ for each SAW sensor into one characteristic spectrum.

Figure 11:
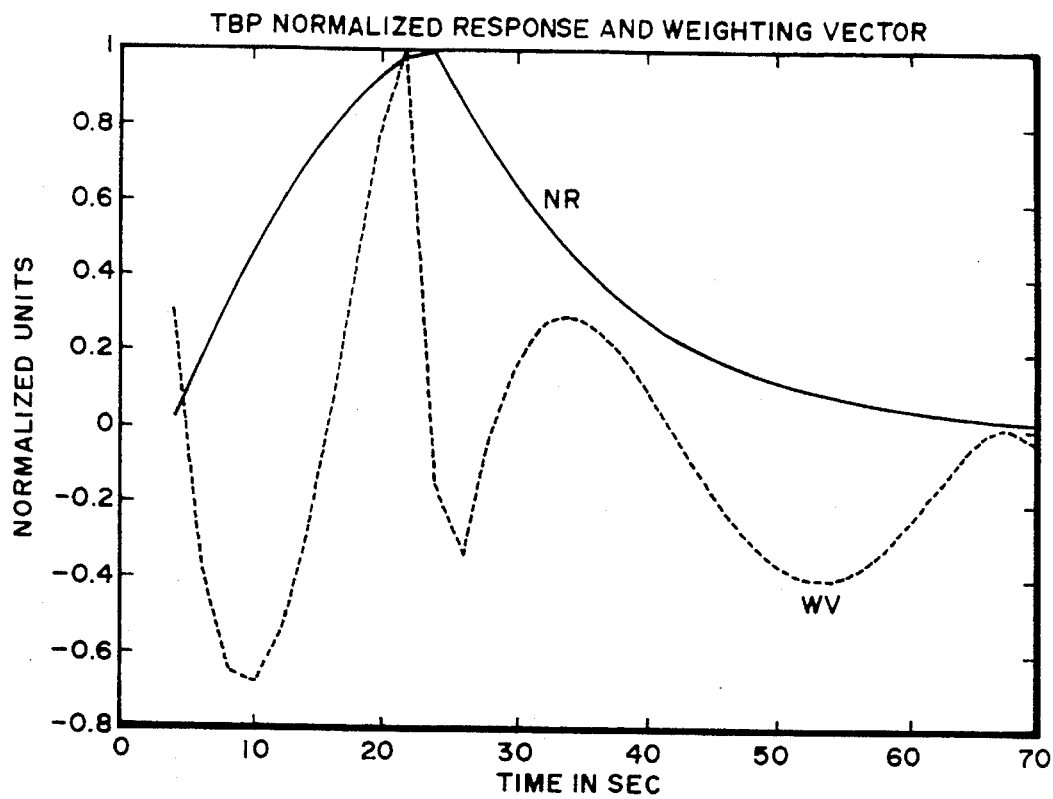
FIG. 11 shows TBP characteristic transients and a corresponding weighting vector (normalized)

FIG. 11 is a plot of normalized instrument response to TBP vs.time, and shows the weighting vectors developed to determine TBP concentration from an arbitrary mixed sample signal. The curve marked NR is a characteristic response of TBP and the curve marked WB is a weighting vector. Both vectors are normalized to unity for display purposes.

Figure 12:
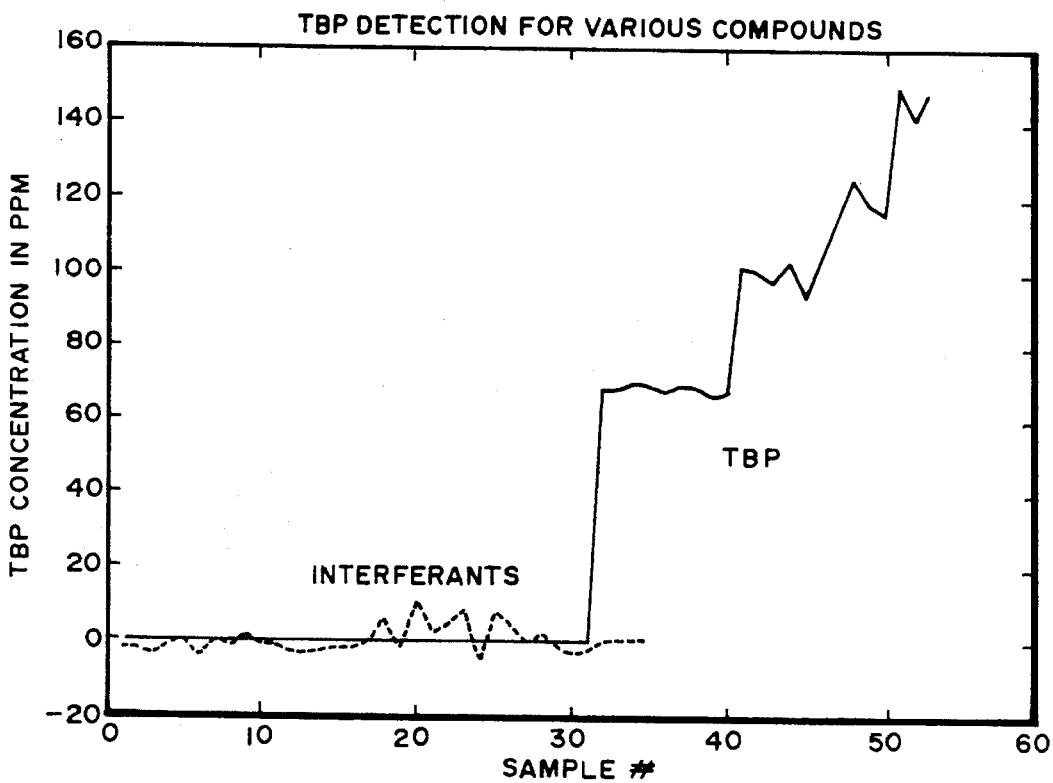
FIG. 12 shows TBP detection for the sample described in FIGS. 7 and 8 using the method and apparatus of this invention.

FIG. 12 is a plot of TBP concentrations vs. sample numbers and thus shows the detection of TBP as a strong signal against all other vapors in the mixture which are referred to as interferants in this figure. For this application, the cross sensitivities of the TBP determination to much higher concentrations (and instrument responses) of interferents, are demonstrated to be small.

We claim:

1. A method for detecting and determining the concentration of at least one target compound in a vapor mixture of compounds of unknown concentrations comprising the steps of:

providing a pair of vapor responsive sensors whose average one cycle frequency response to a unit concentration of a selected vapor is known;

subjecting said vapor responsive sensors to a mixture of compounds of unknown concentrations which provide a frequency shift from said average frequency response to a second frequency response as a result of said mixture on said vapor responsive sensors; and processing this frequency shift by multidimensional statistical methods to detect the target compound and determine its concentration.

2. The method of claim 1 wherein the step of processing the frequency shift comprises:

constructing a calibration matrix comprising vectors that represent the average one cycle frequency response of said vapor responsive sensor per unit concentration of each target compound;

constructing a response matrix comprising the one cycle frequency shift of said vapor responsive sensor to said vapor mixture; and operating on said response matrix by said calibration matrix to calculate the concentration of each target compound.

3. The method of claim 2 wherein the step of operating on said response matrix comprises multiplying said response matrix by the pseudo inverse of said calibration matrix.

4. The method of claim 3 wherein the step of providing a pair of vapor responsive sensors comprises providing a surface acoustic wave sensor.

5. A method of detecting and determining the concentration of a target compound in a vapor mixture containing unknown concentration of the target compound and interferants, comprising the steps of:

providing a surface acoustic wave sensor which has been calibrated to produce a signal which is an average one cycle response per unit concentration of the target compound;

exposing this calibrated sensor to said vapor mixture to produce an output signal; and mathematically processing this output signal to identify the target compound and its concentration in the mixture.

6. The method of claim 5 wherein the step of mathematically processing the output signal of said sensor comprises:

constructing a calibration matrix comprising vectors that represent the average one cycle response of the sensor per unit concentration of the target compound;

processing the output signal of said sensor and said calibration matrix by multidimensional statistical methods to detect the target compound and determine its concentration.

7. The method of claim 6 wherein the step of processing the output signal of said sensor and said calibration matrix includes forming weighting vectors from said calibration matrix and multiplying said weighting vectors by said output signal to obtain a vector representing the concentrations of said target compound in said vapor mixture.

8. A method of detecting at least one target compound and its respective concentration in a vapor mixture having one or more target compounds and interferants, comprising the steps of:

directing sample mixtures containing known concentrations of said target compounds through each of an array of surface acoustic wave sensors to produce output signals which are each processed to provide a set of vectors representing the average one cycle response per unit concentration for each of the target compounds;

constructing a matrix with each of the vectors of target compound response forming the columns of the matrix;

exposing said sensor array to a mixture containing unknown concentrations of one or more of said target compounds to produce an output signal;

mathematically processing this output signal to identify any one or more of the target compounds and their concentrations.

9. The method as claimed in claim 8 wherein the last mentioned step includes forming weighting vectors from the target compound response matrix and using this vector to extract the concentrations of the identified target compounds.

10. The method of claim 9 wherein the step of processing the output signal of said sensor array further comprises multiplying said weighting vectors by said output signal to obtain a vector representing the concentrations of said target compounds in said vapor mixture.

11. The method of claim 8 wherein the step of mathematically processing the output signal of said sensor array to identify target compounds comprises:

processing the output signal of said sensor array to obtain a vapor mixture response matrix comprising a vector for each sensor in said sensor array representing the response of said sensor to the exposure of said vapor mixture; and determining the presence and concentration of target compounds in said vapor mixture by mathematical operations on said vapor mixture response matrix by said target compound response matrix.

12. The method of claim 11 wherein determining the presence and concentrations of said target compounds comprises multiplying said vapor mixture response matrix by the pseudo inverse of said target compound response matrix.

13. The method of claim 8 wherein the step of directing known concentrations of said target compounds through each sensor of said sensor array comprises:

recording the response of each sensor to the known concentration of said target compound; and scaling this response data to obtain a set of vectors representing the average one cycle response of said sensor to a unit concentration of said target compound.

* * * * *